United States Patent [19]

Hudspeth

[11] Patent Number: 5,392,788
[45] Date of Patent: Feb. 28, 1995

[54] METHOD AND DEVICE FOR INTERPRETING CONCEPTS AND CONCEPTUAL THOUGHT FROM BRAINWAVE DATA AND FOR ASSISTING FOR DIAGNOSIS OF BRAINWAVE DISFUNCTION

[76] Inventor: William J. Hudspeth, 415B Sanford St., Radford, Va. 24141

[21] Appl. No.: 13,026

[22] Filed: Feb. 3, 1993

[51] Int. Cl.$^6$ .......................................... A61B 5/0476
[52] U.S. Cl. .................................................. 128/731
[58] Field of Search ........................................ 128/731

[56] References Cited

U.S. PATENT DOCUMENTS

| | | |
|---|---|---|
| 3,087,487 | 3/1961 | Clynes . |
| 3,705,297 | 12/1972 | John . |
| 3,901,215 | 8/1975 | John .................................. 128/731 |
| 4,188,956 | 2/1980 | John . |
| 4,201,224 | 5/1980 | John . |
| 4,279,258 | 7/1981 | John . |
| 4,408,616 | 10/1983 | Duffy et al. ......................... 128/731 |
| 4,411,273 | 10/1983 | John . |
| 4,417,592 | 11/1983 | John . |
| 4,421,122 | 12/1983 | Duffy . |
| 4,462,411 | 7/1984 | Rickards . |
| 4,493,327 | 1/1985 | Bergelson et al. . |
| 4,503,863 | 3/1985 | Katims . |
| 4,545,388 | 10/1985 | John . |
| 4,651,145 | 3/1987 | Sutter . |
| 4,676,611 | 6/1987 | Nelson et al. . |
| 4,705,049 | 11/1987 | John . |
| 4,815,474 | 3/1989 | Duffy . |
| 4,841,943 | 6/1989 | Favreau et al. . |
| 4,844,086 | 7/1989 | Duffy . |
| 4,846,190 | 7/1989 | John . |
| 4,913,160 | 4/1990 | John . |
| 4,926,968 | 5/1990 | Wright et al. . |
| 4,926,969 | 5/1990 | Wright et al. ....................... 128/731 |
| 4,928,704 | 5/1990 | Hardt . |
| 4,941,477 | 7/1990 | Farwell ................................ 128/731 |
| 4,949,725 | 8/1990 | Raviv et al. ......................... 128/731 |
| 4,953,968 | 9/1990 | Sherwin et al. . |
| 4,987,903 | 1/1991 | Keppel et al. ....................... 128/731 |
| 5,003,986 | 4/1991 | Finitzo et al. . |
| 5,113,870 | 5/1992 | Rossenfeld ........................... 128/731 |
| 5,230,346 | 7/1993 | Leuchter et al. .................... 128/731 |
| 5,243,517 | 9/1993 | Schmidt et al. ..................... 128/731 |

OTHER PUBLICATIONS

Klein, "IEEE Transactions on Biomedical Engineering" vol. BME 2343, May, 1976, pp. 246-252.
Walter, "Electronic Engineering", Nov. 1943, pp. 236-240.
Neuropsychologia, 1978, vol. 16, pp. 201 to 212, Neural Models for Short-Term Memory: A Quantitative Study of Average Evoked Potential Waveform, William J. Hudspeth and G. Brian Jones.
The Geometric Representation of Some Simple Structures, Richard L. Degerman pp. 193-211.
A Taxonomy of Some Principal Types of Data and of Multidimensional Methods for Their Analysis, Roger N. Shepard, pp. 21-47.
VEPs and Dimensions of Perception, William J. Hudsepth, Center for Brain Research, Radford University, Radford, Va. (USA), p. 132 of Abstracts submitted to 5th Intl. Conference of Psychology, Budapest, Jul. 1990.
Newspaper article, Fujitsu Labs Tries 'Silent Speech' Input, Dec. 08, 1992.

*Primary Examiner*—William E. Kamm
*Attorney, Agent, or Firm*—Oblon, Spivak, McClelland, Maier & Neustadt

[57] ABSTRACT

A system for acquisition and decoding of EP and SP signals is provided which comprises a transducer for presenting stimuli to a subject, EEG transducers for recording brainwave signals from the subject, a computer for controlling and synchronizing stimuli presented to the subject and for concurrently recording brainwave signals, and either interpreting signals using a model for conceptual perceptional and emotional thought to correspond EEG signals to thought of the subject or comparing signals to normative EEG signals from a normative population to diagnose and locate the origin of brain dysfunctional underlying perception, conception, and emotion.

18 Claims, 10 Drawing Sheets

VISION
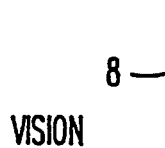
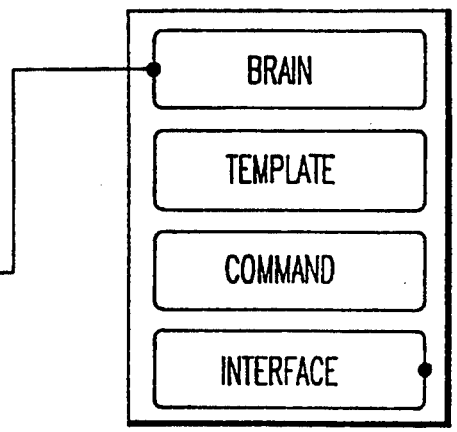
*FIG. 3A*
AUDITION
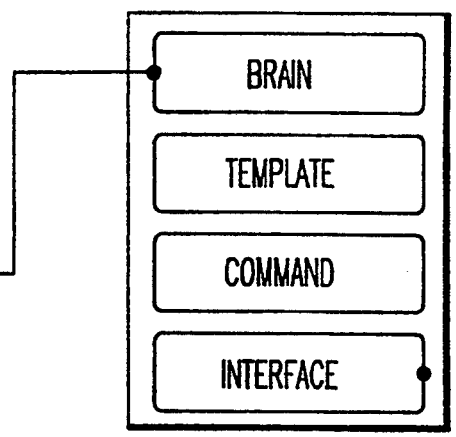
*FIG. 3B*
TACTILE
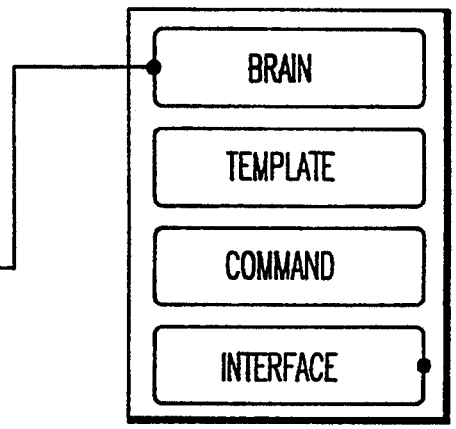
*FIG. 3C*
AUTOCORRELATE
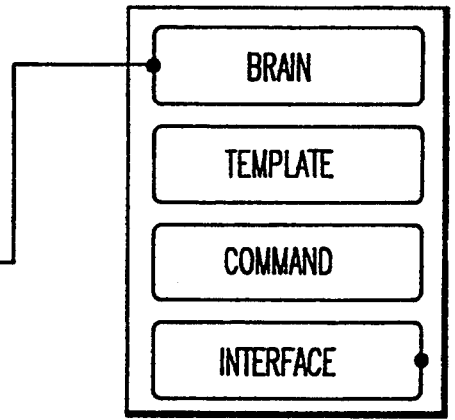
*FIG. 3D*

FIG. 5

|  | RED | GREEN |
|---|---|---|
| TRIANGLE | RED TRIANGLE (RT) WAVEFORM $\alpha_R \vec{V}_{COLOR} + \alpha_\Delta \vec{V}_{SHAPE} = RT$ | GREEN TRIANGLE (GT) WAVEFORM $\alpha_G \vec{V}_{COLOR} + \alpha_0 \vec{V}_{SHAPE}$ | RT−GT = COLOR WAVEFORM $(\alpha_R - \alpha_G) \vec{V}_{COLOR}$ |
| CIRCLE | RED CIRCLE (RC) WAVEFORM $\alpha_R \vec{V}_{COLOR} + \alpha_0 \vec{V}_{SHAPE} = RC$ | GREEN CIRCLE (GC) WAVEFORM $\alpha_G \vec{V}_{COLOR} + \alpha_0 \vec{V}_{SHAPE}$ | RC−GC $(\alpha_R - \alpha_G) \vec{V}_{COLOR}$ |
| | RT − RC = SHAPE WAVEFORM $(\alpha_\Delta - \alpha_0) \vec{V}_{SHAPE} = RC$ | GT − GC = SHAPE WAVEFORM $(\alpha_\Delta - \alpha_0) \vec{V}_{SHAPE}$ | |

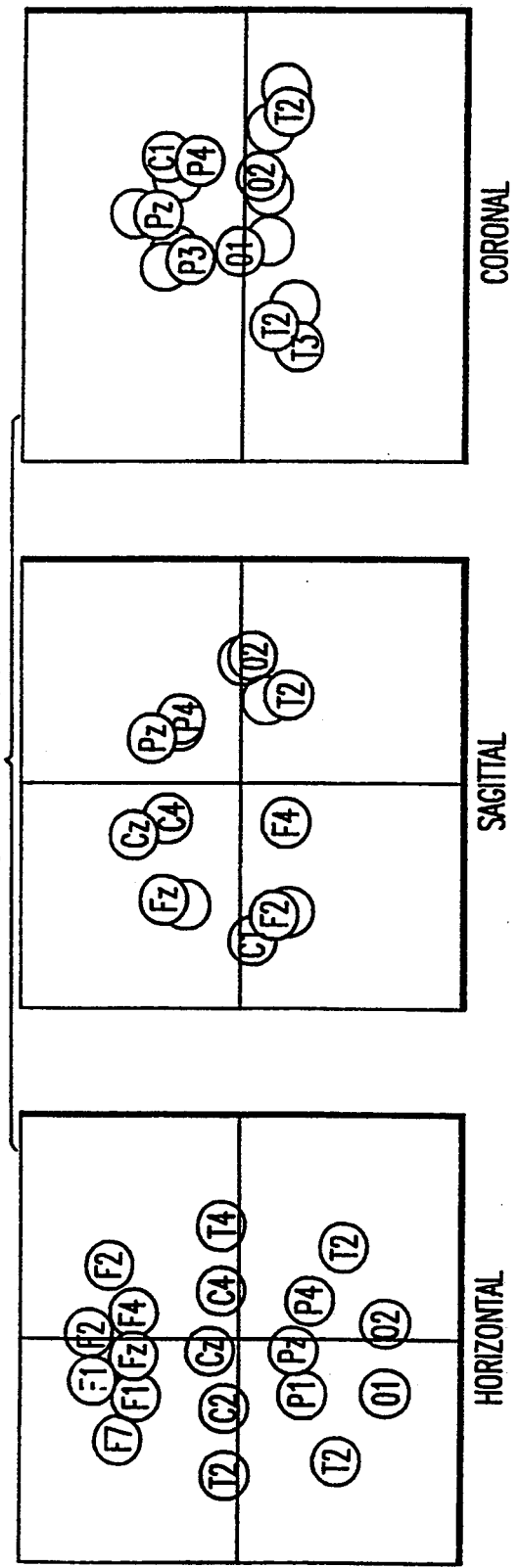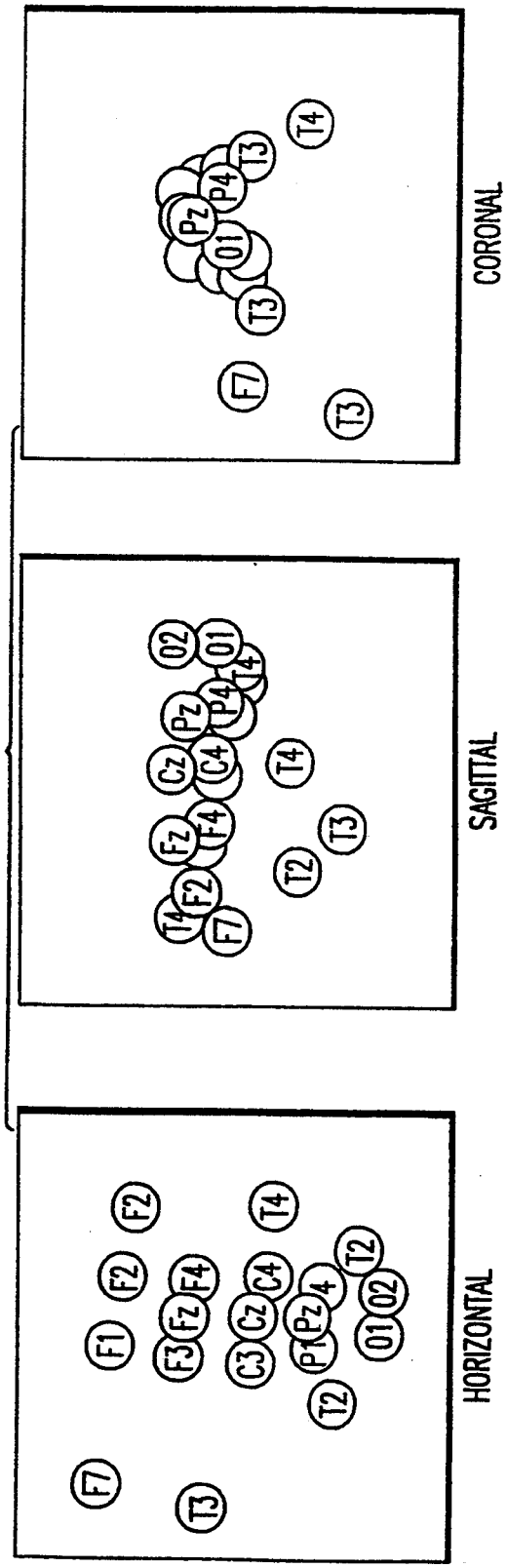
FIG. 8A
FIG. 8B

METHOD AND DEVICE FOR INTERPRETING CONCEPTS AND CONCEPTUAL THOUGHT FROM BRAINWAVE DATA AND FOR ASSISTING FOR DIAGNOSIS OF BRAINWAVE DISFUNCTION

BACKGROUND OF THE INVENTION

1. Field of the Invention

This invention relates to the field of neuroscience and more particularly relates to the application of human brain wave analysis including quantitative electroencephalography. More particularly, the present invention relates to conceptual interpreters and conceptually driven interfaces.

2. Discussion of the Background

Electrical brain activity can be detected using electrodes placed on the scalp of a human subject. An electroencephalogram (EEG) is a recording of a time-varying spontaneous potential (SP) that is obtained from an alert and resting subject. When a subject is presented brief sensory stimuli (e.g., a flash, a click, a mild shock to the skin), a time-varying evoked potential (EP) is superimposed upon the normally present SP so that the EEG voltage includes both SP and EP components. The EP waveform begins within a few milliseconds after receipt of a sensory stimulus, and continues with a decreasing oscillatory magnitude so that it can be distinguished from the SP for as long as one second.

Previous investigations of EP signals have been directed toward methods and devices for distinguishing between normal subjects and subjects with various brain dysfunctions and for use of EP signals to control hardware devices.

Various regions of the brain have different functions and some of those regions are responsible for different types of conceptual functions, such as spatial relationship and word interpretation. When one of those areas of the brain dysfunctions, the specific mental functions associated therewith are impaired.

U.S. Pat. No. 3,901,215 discloses selection of stimuli that are intended to generate different levels of brain function, such as sensory, perceptual, and conceptual function. A neurometric test battery is disclosed in the '215 patent. That test battery includes several stimulus conditions that represent different levels of stimulus complexity. For each stimulus condition, the disclosed neurometric test battery attempts to determine whether the brain of a subject, as indicated by EP waveforms, distinguishes between two exemplars of a similar type. The model used in the '215 patent assumes, however, only that a difference in EP signals received from the brain of a subject while that subject senses different stimuli indicates that the brain of the subject has distinguished between those stimuli. Therefore, the only answer obtainable based upon the model disclosed in the '215 patent is that two stimulus conditions are either the same or different.

U.S. Pat. No. 4,926,969 discloses an EP based control device in which a subject must focus attention on one checkerboard stimulus among a panel of such stimuli. Those stimuli are used to stimulate the receptor system of a subject at different frequencies. When the subject focuses attention on one of the panels, the unique frequency associated with that panel generates a unique EP waveform from the brain of the subject. The unique frequency dependence generated thereby is used to selectively control a hardware device. Different commands may be issued to the device depending upon which checkerboard the subject stares at. Using that system, the subject must attend to a computer display representing a desired control command. The '969 patent explicitly (see column 8, lines 34-41) avoids using complex stimuli such as size, color, and shape.

SUMMARY OF THE INVENTION

Accordingly, one object of this invention is to provide a novel system that can be used to determine from brainwave recordings from a subject whether translation of external stimuli has occurred.

Another object of this invention is to provide a novel system for determining from the brain waves of a subject whether conception, perception, or emotion has occurred in that subject.

Another object of the invention is to provide a novel system for determining functionally damaged areas of the brain of a subject and to determine what type of functional damage has occurred.

Another object of the invention is to provide a novel hardware control device that can be regulated by brain waveforms corresponding to predetermined thoughts.

Another object of the invention is to provide a hardware control device than can be regulated by EP waveforms induced by either external stimuli or by imagination of a subject.

These and other objects of the invention are provided by a novel system for the acquisition and decoding of EP and SP signals, which comprises a transducer for presenting stimuli to a subject, EEG sensors for recording brainwave signals from the subject, a computer for controlling and synchronizing stimuli presented to the subject and for concurrently recording brainwave signals. The computer also provides means to decode the content of the brainwave signals according to a stimulus model for perceptual, conceptual, and emotional translations.

The invention also provide a novel SP source locator method for determining whether regions of the brain of a subject are functional or dysfunctional, by recording a plurality of SP waveforms from a plurality of scalp locations, determining three basis waveforms from the SP waveforms, along three orthogonal axes. Each of the basis waveforms provide a best fit to the variation in SP waveform along one of the orthogonal axes so that the most complete representation of all the SP waveforms by linear combinations of the three basis waveforms is provided. A coordinate for each SP waveform consisting of the three coefficients for the three basis waveforms representing that SP waveform is plotted, forming a three dimensional plot. That plot is compared with a similar plot representing normative values obtained from a large population of subjects, wherein deviations of the position of a coordinate corresponding to an electrode from a normative value position indicates that a functional region of the brain adjacent to said electrode position is dysfunctional.

I have discovered that the brain interprets sensory stimuli to have perceptual conceptual or emotional meaning, that according to certain rules which indicate whether the stimuli have perceptual, conceptual, or emotional meaning, that EEG signals from the brain encode the type of interpretation of stimuli which the brain has made, and that similar EEG signals occur if an individual imagines an interpreted stimulus instead of experiencing that stimulus. Certain terms must be defined to adequately describe the discoveries and the corresponding inventions. Those definitions along with a more detailed discussion of the discoveries and the inventions follow.

I have discovered that the brain makes distinctions between stimuli based upon whether those stimuli have perceptual, conceptual, or emotional meaning to the brain, and that the brain does so based upon predetermined rules that the brain uses for interpreting real world stimuli external to the subject. External stimuli are defined to mean stimuli which are perceived via a sensory system of the body of the subject, as opposed to imagined stimuli.

There is a hierarchy of brain interpretation. The brain attempts to interpret stimuli at the highest hierarchical level. Conceptual interpretation is higher in the hierarchy than perceptual interpretation which is higher in the hierarchy than emotional interpretation which is higher in the hierarchy than the simple sensory information that impinges upon the subjects sensory receptors.

I define use of the different rules used by the brain for interpreting stimuli as translations. The brain translates sensory input from external stimuli using the highest hierarchical interpretation in order to understand the real world. Translations are based upon stimulus attributes that a subject can understand and interpret. An attribute is defined to be a common feature that can be shared by more than one stimulus. An exemplar of an attribute is defined to be a particular example of that attribute. A stimulus set is defined to be a set of a stimuli which have a set of attributes with particular exemplars. An example of an attribute is color, and color has as exemplars red, green, blue, etc. Each stimulus exemplar may have more than one attribute associated with it. A stimulus set can be formed from stimuli that have selective translations that are based upon conceptual, perceptual or emotional attributes.

Conception is defined to mean that the interpretation of stimuli is based upon common symbolic and object attributes in a stimulus set. For instance, words and pictures are each symbol systems that can, for example, be used to represent objects such as cat and dog. The brain classifies information according to similarities and differences in the symbolic and object attributes represented in the stimulus set. For example, each stimulus may use a word attribute and at the same time an object attribute. Alternatively, each stimulus may use a picture attribute and at the same time an object attribute. The brain concludes that the words and pictures for the same object are equivalent. At the same time the brain concludes that words belong to a common symbol system and that pictures belong to a common symbol system which is distinct from a word symbol system.

Perception is defined to mean that the interpretation of stimuli is based upon common, nonsymbolic, pattern attributes in a stimulus set. The brain classifies information according to similarities and differences in the texture and color attributes represented in a stimulus set. For example, each stimulus may use a texture attribute and at the same time a color attribute. The brain must be able to conclude that the color red is equivalent when associated with fine or coarse checkerboard stimuli, and at the same time the brain must be able to conclude that the color green is equivalent when associated with fine or course checkerboard stimuli in order to classify according to red or green. Similarly, the brain concludes that a coarse checkerboard texture is equivalent when associated with red or green stimuli, and at the same time the brain concludes that a fine checkerboard texture is equivalent when associated with red or green stimuli when classifying coarse and fine checkerboard texture.

Emotion is defined to mean that the interpretation of stimuli is based upon common emotional and situational attributes in a stimulus set. The brain classifies information according to similarities and differences in the emotional and situational attributes represented in the stimulus set. Each stimulus may use a situational attribute and at the same time an emotional attribute. For example, the brain concludes that male and female faces that depict smiles can be interpreted as an equivalent happy emotion. Alternatively, the brain concludes that male and female faces that depict anger can be interpreted as an equivalent angry emotion. At the same, the brain concludes that male faces are equivalent when associated with happy or angry emotions, and that female faces are equivalent when associated with happy or angry emotions.

A stimulus model is a model which represents attributes as orthogonal vector directions in a vector space and represents an exemplar of an attribute as a vector of a particular magnitude along the vector direction of its attribute.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 1 and 1A show a system for correlating brainwaves to the thoughts of a subject;

FIG. 3 shows three types of NCP systems for presenting auditory, visual, and tactile simulation, and also a system without a NCP;

FIG. 5 shows mathematical relationships of a stimulus model among orthogonalized stimulus attributes for the stimulus set of FIG. 4B;

FIGS. 8A–8C show three SP structure diagrams representing a normative subject, a subject having temporal disconnection-closed head trauma and a subject with posterior interhemispheric disconnection-right occipitoparietal tumor resection.

DESCRIPTION OF THE PREFERRED EMBODIMENTS

Figure 1:
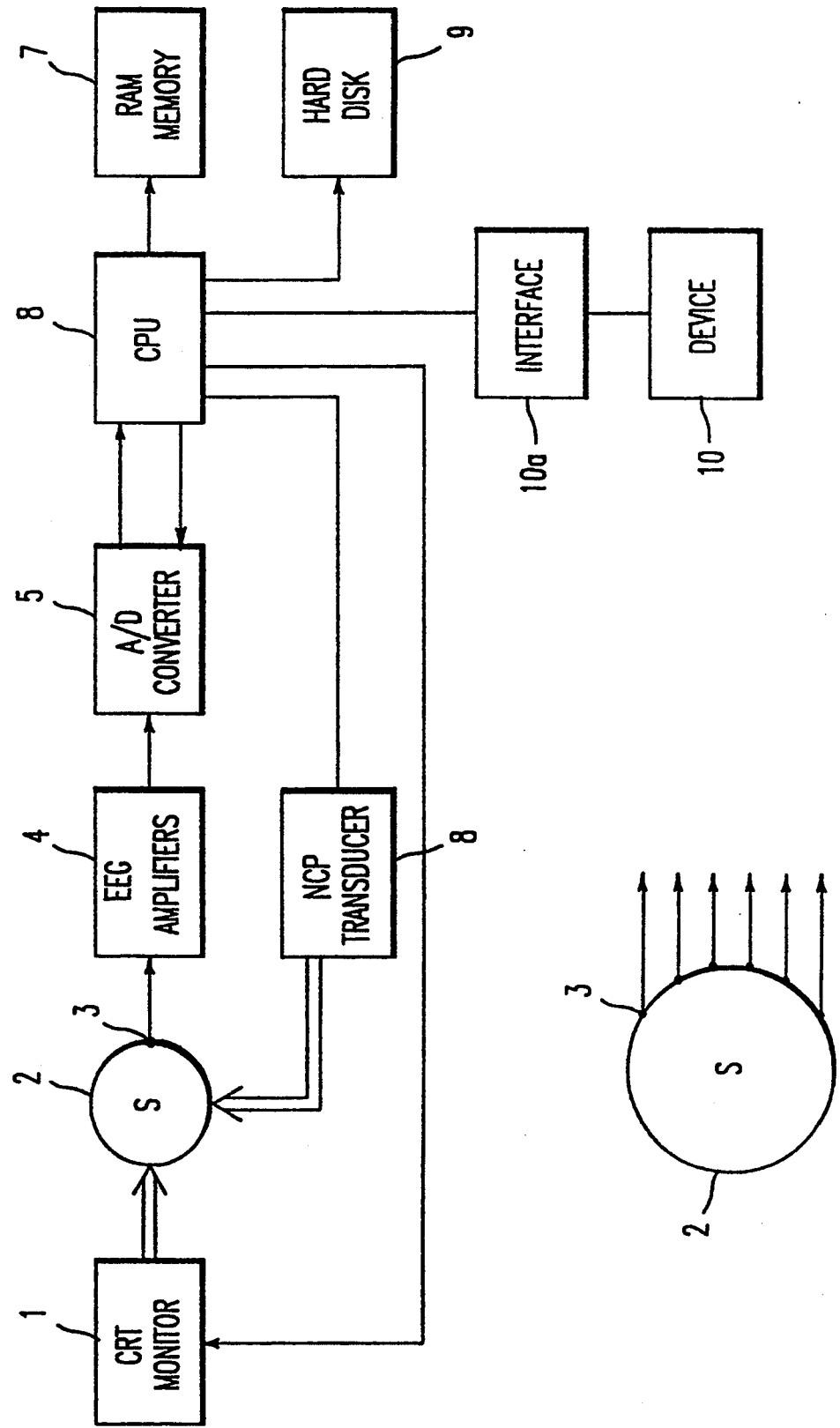

Referring now to the drawings wherein like reference numerals designate identical or corresponding parts throughout the several views and more particularly to FIG. 1 thereof which shows a novel system of the invention which includes CRT monitor 1 for presenting conceptual information to subject 2. CRT monitor 1 may be replaced by any transducer for sounds and touch. Microvolt level EEG signals of either the SP or EP type from subject 2 are measured with EEG electrodes 3 and amplified with an EEG amplifier 4. EEG amplifier 4 is coupled to an analog-to-digital converter 5 that transmits digitized versions of EEG signals to the central processing unit (CPU) 6. CPU 6 is coupled to random access memory (RAM) 7 and to hard disk 9 for storing and retrieving information. CPU 6 is also coupled to a non-contingent probe (NCP) transducer 8 for providing brief and meaningless background stimuli to subject 2.

NCP stimuli are defined to be brief and meaningless stimuli that are identical to one another and applied to any of the sensory systems of a subject. NCP stimuli are used to generate EP waveforms. When no other stimuli are being presented to a subject, NCP stimuli evoke EP waveforms and the EP waveforms evoked by an NCP stimuli at one time are very similar to NCP evoked EP waveforms which are evoked at another time.

Although FIG. 1 shows a single system for both presenting conceptual stimuli to subject 2 and for controlling device 10, it is clear to one of ordinary skill in the art that those functions may be provided in separate devices.

FIG. 1A shows an alternative embodiment including a plurality of EEG recording electrodes 3 used to obtain simultaneous recordings of SP and/or EP signals from a plurality of locations on the head of subject 2.

Figure 2:
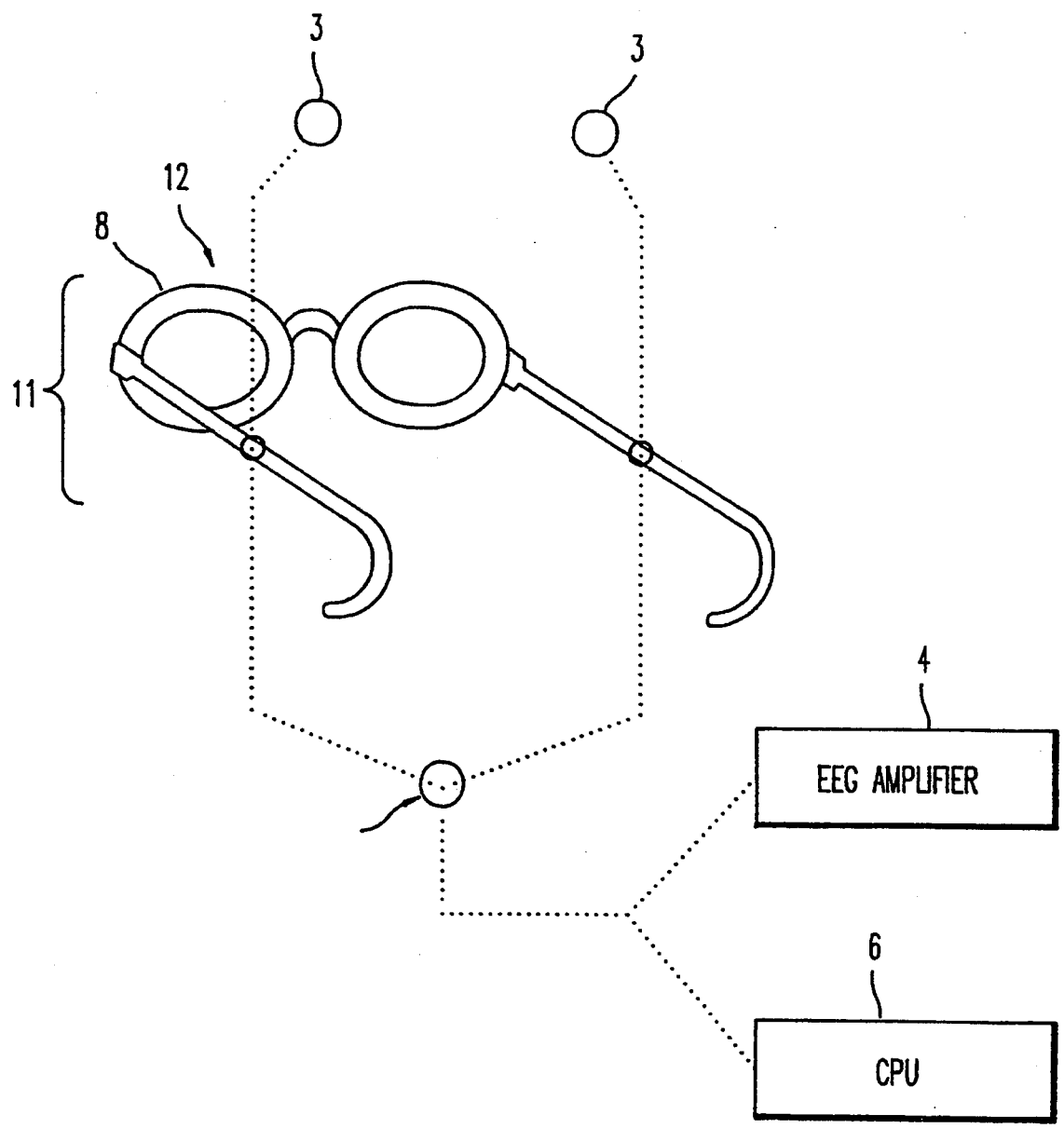
FIG. 2 shows a system for providing NCP stimuli to a subject while recording EP signals from that subject.

FIG. 2 shows a presently preferred embodiment for providing visual NCP stimuli to subject 2 and for recording EP waveforms from subject 2. FIG. 2 shows eyeglass frame 11 which includes annular rims 12 that contain NCP transducer 8. NCP transducer 8 may be an array of LCD's or an array of LED's, as indicated by hashed areas on annular rim 12. In either case, NCP transducer 8 provides a brief background flash in order to evoke an EP waveform. That evoked EP waveform reflects the brain state of subject 2. Brain state is defined as the sum of EP waveform components including an EP waveform representing the background NCP stimuli and an EP waveform component corresponding to the perceptual, conceptual or emotional translation of experience. Experiences are defined to mean either external stimuli received by subject 2 or stimuli imagined by subject 2. EP waveforms are recorded from electrodes 3 concurrent with the presentation of NCP stimuli. Electrical wires connecting NCP transducer 8 and EEG electrodes 3 to the rest of the system are illustrated by dotted lines.

FIG. 3 schematically shows that NCP transducer 8 need not be limited to visual stimulation. NCP transducer 8 may optionally stimulate any one or all of the sensory systems of subject 2. Visual, auditory, and tactile NCP stimuli may produce different EP waveforms and may produce different template waveforms from one another. However, in all cases shown in FIG. 3, the same algorithms may be used to record EP waveforms, to compare incoming EP waveforms with predetermined template waveforms, an to generate commands to activate an interface device.

FIG. 3 also shows an autocorrelate mode in which no NCP stimuli are presented and only an SP waveform is recorded as a function of time. In that case, short time records of EEG signals are recorded with a recording frequency of between 1 and 10 Hz and analyzed to determine whether their waveforms correspond to the stimulus model discussed below. In an autocorrelate mode the stimulus model waveforms are SP waveforms.

The system of the invention also includes a correlator with which to determine whether a series of raw EP waveforms from a subject are similar to a set of stored EP waveforms, called template or TEP waveforms that correspond to waveforms generated by a predefined set of attributes. The correlator may comprise a program implemented via the CPU, and memory. Alternatively, the correlator may comprise a hardwired special purpose portion of CPU 6, an EPROM, or a similar hardware device. Predetermined TEP waveforms may be stored as data files on hard disk 9 or may be stored in a ROM. When a high correlation of an EP waveform received from the brain of a subject with one of the TEP waveforms stored in memory of the correlator exists, the system issues a command corresponding to the correlated TEP waveform. That command may be used to control a device to perform a specified function.

TEP waveforms for subject 2 are determined prior to cybernetic control of device 10 by subject 2. TEP waveforms are determined in accordance with a stimulus model for a stimulus set. A different stimulus model is prepared for each stimulus set. The stimulus model represents the attributes of a stimulus set. The brain recordings are corresponded with a set of basis waveforms which are sufficient in number to span the number of attributes embodied in the stimulus set.

The stimulus model along with a method for determining what waveforms and magnitudes correspond to the basis waveforms and magnitudes for attributes and exemplars enable decoding of the content of the recorded brainwave signals to indicate what translations have occurred in the brain. As discussed, that model represents attributes of the stimulus set as orthogonal waveforms which form a basis set of waveforms. Different amplitudes for an attribute represent different exemplars of that attribute. That basis set of waveforms along with a background basis waveform of the model span the function space of EP waveforms for the stimulus set.

A stimulus set is chosen to include stimulus exemplars so that every member of the set has at least two attributes in common with other members of the set. Preferably, each set includes at least four stimuli and at least two attributes. A stimulus model for that stimulus set models each stimulus exemplar with orthogonal basis vectors having a sign and magnitude uniquely associated with the attributes used in the set. Next, correspondence between the sign and magnitude of waveforms and exemplars is determined.

A waveform corresponding to an attribute is defined to be an attribute waveform. A magnitude of an attribute waveform corresponding to an exemplar magnitude is defined to be an exemplar magnitude of an attribute waveform.

The stimulus model attribute waveforms and exemplar magnitudes which correspond to the basis vectors of the stimulus model for subject 2 may be determined by presenting the stimuli of a stimulus set to subject 2 while recording waveforms from the brain of subject 2, equating linear combinations of the attribute waveforms with exemplar magnitude coefficients corresponding to the model attributes and exemplars of each stimulus to the waveform recorded from the brain of subject 2 for that stimulus, and then solving for the attribute waveforms and exemplar magnitudes using the linear equations obtained for the stimuli.

Once the attribute waveforms and exemplar magnitudes for the exemplars of the model have been determined they are stored in memory. With those predetermined stored values subject 2 may use the system described with reference to FIG. 1 to control device 10.

However, it is useful to proceed with a training method for training subject 2 to improve his control of the system of FIG. 1.

During training of subject 2 to control device 10, CPU 6 displays a conceptual stimulus (i.e., a stimulus which has symbolic meaning) on CRT monitor 1 and simultaneously delivers a continuous train of NCP stimuli to subject 2. EP signals from subject 2 generated by attention of subject 2 to that stimulus while subject 2 is subjected to an NCP stimulus are recorded and compared with predetermined TEP waveforms. When a high correlation between the EP and TEP waveforms occurs subject 2 is notified e.g., via feedback from device 10. In this training phase device 10 may be a device which produces an audible or visual signal in response to high correlation. After this training phase CRT 1 is extraneous and may be removed.

When subject 2 controls device 10, device 10 is coupled through interface 10A to CPU 6. Device 10 is activated by commands from CPU 6 which are generated in response to high correlations between NCP induced EP waveforms generated by subject 2 and predetermined stored template EP (TEP) waveforms stored in RAM 7 or on hard disk 8.

In the presence of external stimuli or imagined stimuli, EP waveforms evoked by a constant NCP stimuli may be represented by the linear superposition of orthogonal basis waveforms of the stimulus model. A background basis waveform corresponds to the constant background NCP stimuli and the additional basis waveforms correspond to the attributes of the model. After an external stimulus or imagined stimuli an EP evoked by an NCP stimuli contains amplitude for basis waveforms corresponding to attributes of the external stimulus or imagined stimulus, so long as the NCP occurs while symbolic attributes provided by the external stimulus or thought remain in memory.

In principle, a single NCP pulse may be applied and a single EP waveform recorded. The EP waveform is recorded during a short period subsequent to the NCP pulse and preferably within the first half second after the NCP pulse. Preferably, the NCP stimulus is repeated with a frequency of between 1 and 10 Hz. EP signals are recorded synchronously with generation of NCP pulses in order to segment the time history of experiences of subject 2.

The present invention also provides a novel diagnostic method for diagnosing brain dysfunction using the system disclosed above. The diagnostic method presents diagnostic stimuli sets such as each of the stimuli sets shown in FIGS. 4A-4J in order to provide information regarding brain function.

Each of FIGS. 4A-4J show a minimum stimulus set which is defined to be a set of four stimuli, each stimulus has associated with it two exemplars, each exemplar being an exemplar of one of two attributes. A stimulus model (i.e., mathematical representation) of a minimum stimulus set has two basis vectors which each represent one of the two attributes of the minimum stimulus set. An EP evoked from the brain of a subject while that subject views one of the stimuli of a minimum stimulus set is represented by a linear combination of two basis waveforms corresponding to the two attributes of the set, and also by a third background basis waveform. The third basis waveform is defined to be the background basis waveform of the EPs from that subject. The coefficients of the basis waveforms for the two attributes indicate the presence or absence of exemplars for those attributes in the stimulus generating the EP. If the brain of a subject interprets and translates a stimulus set according to conceptual rules, then the EP waveforms for those stimuli may be represented by a linear combination of two orthogonal basis waveforms, which correspond to translation and interpretation, i.e., attaching meaning to the stimuli, plus the background basis waveform.

The diagnostic method determines from EP waveforms for subject 2 whether subject 2 translates perceptual, conceptual or emotional stimuli according to a stimulus model, for each stimulus set. Reliable and repeatable translations indicate that the brain of subject 2 functions normally.

Figure 4A:
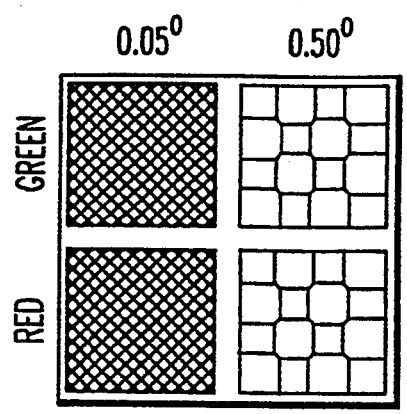
FIGS. 4A–4J show ten different stimulus sets that employ orthogonalized attributes.

FIG. 4A shows four stimulus exemplars which have as attributes check size and color. Small and large checkerboards having green and red colors occur in the four stimulus exemplars.

Figure 4B:
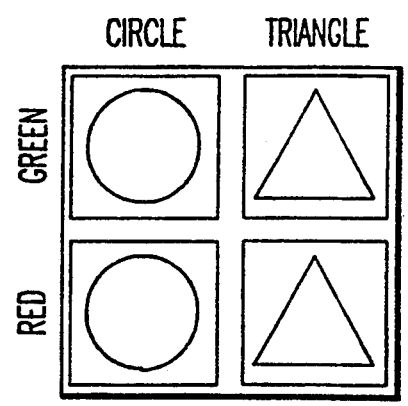

FIG. 4B shows four stimulus exemplars which have as attributes form and color. Circles and triangles having green and red colors occur in the four stimulus exemplars.

Figure 4C:
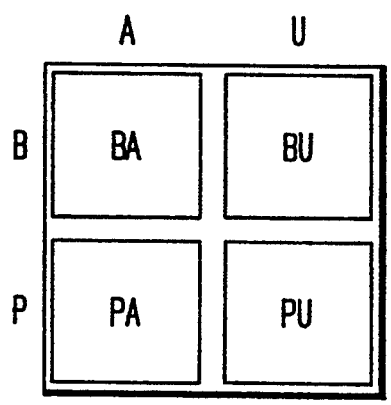

FIG. 4C shows four phoneme stimulus exemplars which have as attributes the initial consonants B and P and the ending vowels A and U. Initial consonants B and P having ending vowels A and U occur in the four stimulus exemplars.

Figure 4D:
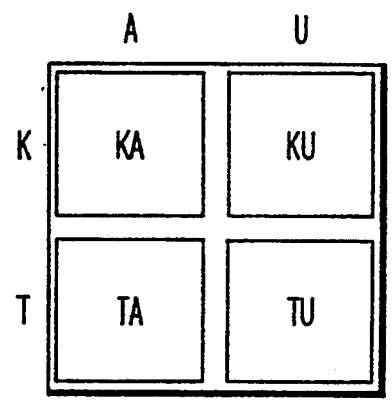

FIG. 4D shows four phoneme stimulus exemplars which have as attributes the initial consonants K an T and the ending vowels A and U. Initial consonants K and T having ending vowels A and U occur in the four stimulus exemplars.

Figure 4E:
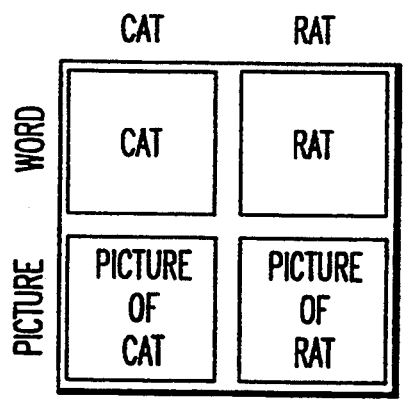

FIG. 4E shows four stimulus exemplars which have as attributes words and pictures of objects. Words and pictures of CAT and RAT occur in the four stimulus exemplars.

Figure 4F:
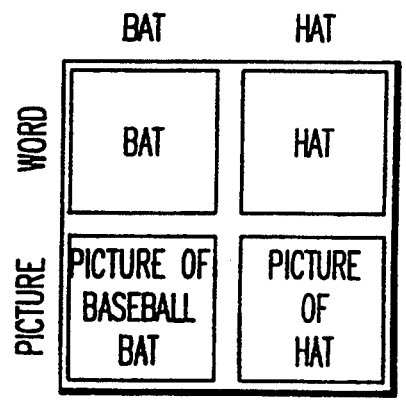

FIG. 4F shows four stimulus exemplars which have as attributes words and pictures of objects. Words and pictures of BAT and HAT occur in the four stimulus exemplars.

Figure 4G:
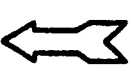

FIG. 4G shows four stimulus exemplars which have as attributes words and pictures for the actions READ(ing) and WRITE(ing). The words for and pictures of a human in the act of READ(ing) and WRITE(ing) occur in the four stimulus exemplars.

Figure 4H:

FIG. 4H shows four stimulus exemplars which have as attributes words and pictures for the actions FEED(ing) and FIGHT(ing). The words for and pictures of a human in the acts of FEED(ing) and FIGHT(ing) occur in the four stimulus exemplars.

Figure 4I:

FIG. 4I shows four stimulus exemplars which have as attributes words and pictures for the spatial orientations LEFT and RIGHT. The words for and pictures of arrows that indicate the spatial orientations LEFT and RIGHT occur in the four stimulus exemplars.

Figure 4J:

FIG. 4J shows four stimulus exemplars which have as attributes words and pictures for the spatial orientations ABOVE and BELOW. The words for and pictures of arrows that indicate the spatial orientations ABOVE and BELOW occur in the four stimulus exemplars.

Each set of stimuli shown in each of FIGS. 4A-4J are used in a neuropsychometric test battery designed to determine whether the brain of subject 2 can translate the types of similarities and differences among the attributes embodied in the stimulus exemplars in each set. It is clear to one of ordinary skill that the neuropsychometric test battery extends to other sensory and motor systems. Emotions such anger, joy, sadness, happiness, depression, elation, and fear are all attributes that can be conveyed by stimuli and therefore categories of translations corresponding to emotive symbolism may also appear in the stimulus model of the present invention. It is also clear to one of ordinary skill that categories of translations can be established for cross-modal functions that entail more than one sensory or motor system. For example, visual and auditory sensory input may be used to provide meaningful signals for translation.

The neuropsychometric test battery comprises an algorithm for presenting various stimuli sets, such as the stimuli sets shown in FIGS. 4A–4J, to a subject in order to determine what types of translations that subject is capable of. A presently preferred embodiment for algorithms of the neuropsychometric test battery will be described with reference to FIG. 1 and with reference to the computer program listing in Appendix A at the end of this specification. The preferred test battery algorithm includes an EP acquisition routine and an EP analysis routine, such as routines IV.A.2 and IV.A.3 listed in Appendix A.

The EP acquisition routine first initializes system variables NSTIM=4 (number of stimuli in set), NREP=80 (number of times each of the NSTIM stimuli is to be presented), and R_STP=0 (pointer to NSTIM arrays that contain the graphic image for each stimulus). Next, the subroutine LOAD_R reads from disk and loads NSTIM graphic images into RAM so that the images can be displayed on CRT 1. Next, the first of the NSTIM stimuli is flashed on CRT 1, and at the same time, A/D converter 5 begins sampling from the EEG amplifiers. The flashed stimuli generates an EP in the brain of subject 2. A/D converter 5 repeatedly samples the EEG amplifier outputs for up to one second to construct an EP waveform. The EP is recorded by subroutine READ_EP and it is then saved by routine SAVE_EP. Then, NREP is decremented by one. The steps above are repeated until NREP=0. Then NSTIM is decremented by one and R_STP is incremented to point to the second stimulus image in the set. The routine then loops through NREP sequences for the second stimulus, and continues to decrement NSTIM, and increment R_STP, until NSTIM=0 and 80 EP waveforms have been saved for each of the four stimuli. The routine then automatically terminates acquisition. The same procedures are automatically applied to EP waveform data from all recording electrodes 3. The acquisition routine can then be repeated for all remaining stimulus sets of the neuropsychometric battery. In Principal Components Analysis the background basis waveform is defined as the principal component and the remaining basis waveforms are defined as unique components. The background waveform, or principal component, must be substracted from each of the four EP waveforms to obtain the unique EP waveforms that correspond to the desired perceptual, conceptual and emotional translations that have occurred due to the stimuli.

The saved EP data are analyzed in the EP analysis routine, which proceeds as follows. The system variables are initialized, NSTIM=4 and NREP=80. The analysis routine then reads NREP EP waveforms for the first stimulus from hard disk, and accumulates a sum of the first set of EP waveforms in RAM. The analysis routine then loops to decrement NSTIM, reads NREP EP waveforms for each of the remaining stimuli from hard disk and accumulates summed EP waveforms for each stimulus in RAM. When NSTIM=0, the routine has completed four summed EP waveforms for each of the NSTIM stimuli. Each summed EP waveform is then normalized by dividing by NREP to construct an averaged EP waveform for each stimulus. These calculations are automatically applied to EP waveform data from all recording electrodes 3.

The STRUCTURE routing is used to construct EP_Structures for each recording electrode. The four averaged EP waveforms represent the brain's response to a stimulus set. The four EPs are modelled by a mathematical representation in which a perceptual or conceptual attribute in a stimulus set evokes a basis waveform. The presence of a second independent attribute evokes a second basis waveform. In the most general sense, the EP waveform can be defined as the linear superposition of k orthogonal basis waveforms which are sufficient in number to represent k attributes. Orthogonal means that the squared correlation coefficient between each pair of k basis waveforms, $r^2$, is <9%.

All the stimulus sets in the neuropsychometric test battery use stimuli which each have two attributes. For each attribute there are two exemplars. For example, in FIG. 4B, there are form and color attributes. Each attribute is modelled in the stimulus model by an orthogonal basis waveform. Each orthogonal basis waveform has a contribution of equivalent magnitude so that the equal weighted sum of the two basis waveforms provides a waveform which is identical to the original EP waveform.

For any stimuli, there is a background basis waveform which corresponds to the reaction of the brain to energy fluctuations presented by that stimulus. That background basis waveform is the same shape for each stimulus in a stimulus set and does not contain any information regarding attributes of the stimuli or translations performed by the brain. That background basis waveform is the arithmetic average of the four EP waveforms generated for a stimulus set of the neuropsychometric test battery. In Principal Components Analysis the background basis waveform is defined as the principal component and the remaining basis waveforms are defined as unique components. The background waveform, or principal component must be subtracted from each of the four EP waveforms to obtain the unique EP waveforms that correspond to the desired perceptual, conceptual or emotional translations that have occured due to the stimuli.

FIG. 5 shows, in tabular form, a mathematical model for the stimulus set shown in FIG. 4B. That model applies to all the 2×2 stimulus sets shown in FIGS. 4A–4J. FIG. 5 shows that EP waveforms for each of the objects having shape and color attributes in FIG. 4B is modelled as a linear combination of shape and color basis vectors.

For any pair of stimulus exemplars that have the same attribute the EP waveform generated by those stimuli have the same basis waveform that are equal in magnitude and have the same sign. However, any pair of stimulus exemplars that represent opposing attributes in the neuropsychometric test battery have the same basis waveform that are equal in magnitude and opposite in sign.

All the 2×2 orthogonal stimulus sets of the neuropsychometric test battery may be modelled in a stimulus model having two orthogonal basis waveforms corresponding to two attributes and two coefficients with opposing signs, with each attribute represented by two exemplars for that attribute.

The four EP waveforms generated by the four stimuli of a stimuli set of the neurocybernetic battery may be graphically represented on the circumference of a unit circle by means of the coefficients for each of the basis waveforms corresponding to each of the four stimuli.

Figure 6:
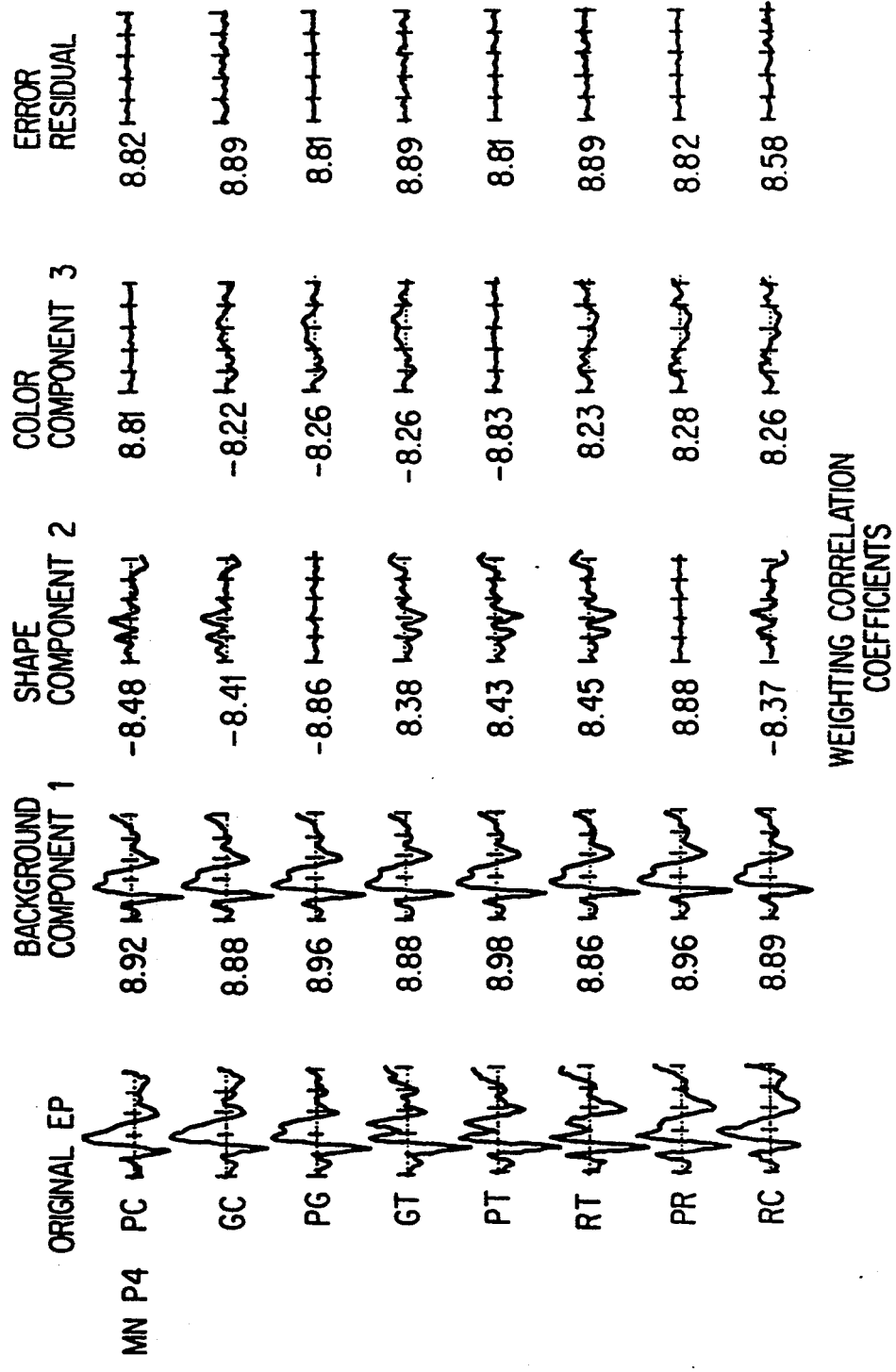
FIG. 6 shows EP waveforms recorded from a subject when that subject viewed the stimulus set shown in FIG. 4B.

FIG. 6 graphically illustrates an analysis of EP waveforms generated in response to the stimuli shown in FIG. 4B. The left-hand column of FIG. 6 shows the original EP waveforms and basis waveforms indicated by columns labeled component 1, component 2, and component 3. Also shown in the right-hand column are the residual magnitudes of the EP waveforms which cannot be represented by a linear combination of the first, second, and third basis waveforms. The numbers adjacent to each of the waveforms shown in the second through fifth columns indicate the coefficients for each of those waveforms necessary to most accurately represent the original EP waveforms shown in the left-hand column. As can be seen in FIG. 6, the waveform shown in the column labeled component 1, which does not correspond to translation, is almost identical for all stimuli of the stimuli set. The preferred embodiment routinely removes an average background EP waveform corresponding to the average value for all the waveforms shown in the column labeled component 1, prior to analyzing EP waveforms for translations.

The neuropsychometric test battery determines whether the brain of a subject 2 can perform translations corresponding to recognition of the attributes existing in a particular stimuli set. More than two attributes may exist in a particular stimulus set in which case more than two basis waveforms corresponding to those attributes exist and are included in the model of the stimulus set.

Different individuals have different EP waveforms for the same stimuli. Therefore, the unique EP waveforms of a subject must be determined for that subject.

When subject 2 imagines a stimulus (i.e., that is when no external stimulus is presented but the subject imagines such a stimulus) while an NCP stimulus is presented the generated EP waveform includes a basis waveform corresponding to the imagined stimulus. Furthermore, the basis waveform so generated is the same basis waveform that occurs when subject 2 views on CRT monitor 1 the same stimulus which was imagined. In other words, when subject 2 perceives, conceives or emotes, either due to external stimuli or due to imagined stimuli, the same basis waveforms are produced.

The present invention provides a novel method of training an individual to use NCP stimuli in conjunction with the imagination of subject 2 in order to control a neurocybernetic device. That training method trains subject 2 to improve correlation between translations that occur due to imagined stimuli and due to external stimuli. The training method for NCP includes providing biofeedback indicative of the level of correlation obtained between an EP generated due to imagination for a particular stimuli and the corresponding stored template EP which had been stored in response to a previous presentation of that external stimuli to subject 2. However, the training proceeds in two phases.

First, subject 2 is trained to improve correlation between EP waveforms generated in response to an external stimuli and previously recorded responses to the same external stimuli. Next, subject 2 is trained to increase the correlation between EP waveforms generated in response to imagination of a stimuli and stored TEP waveform stored in response to the viewing by subject 2 of the corresponding external stimuli.

The present invention also provides a novel diagnostic feedback method for improving reliability of translation which have been indicated to be unreliable by the diagnostic method.

For the diagnostic feedback method, hardware device 10 comprises a feedback device which, for instance, generates an audible beep or a visual flash to inform subject 2 when high correlations occur between corresponding EP waveform and a TEP waveform for a stimulus of a stimulus set which subject 2 does not reliably translate. The diagnostic feedback method provides a neurocognitive rehabilitation method to train subject 2 to improve translations of perceptual, conceptual and emotional stimuli.

Neurocognitive rehabilitation allows subject 2 to provide higher correlations between a stored template waveform indicative of translation of a stimulus and EP waveforms generated by subject 2 in response to being stimulated by that stimulus. Since higher correlation between stimulus EP waveforms and prerecorded template waveforms improves the reliability of control of external hardware device 10, the rehabilitative process discussed above improves the utility of a neurocybernetic device of the present invention.

By using feedback, the subject may increase the correlation between EP waveforms and predetermined TEP waveforms in order to provide higher reliability in issuing of commands so that those commands are only issued when corresponding perceptual, conceptual or emotional translations occur and those commands are not issued when corresponding perceptual, conceptual or emotive translations do not occur. The correlation between the EP and TEP waveforms may be defined by, for instance, by the Pearson product-moment correlation coefficient. The absolute correlation value required to issue a command to device 10 may be set to a level providing high reliability.

The invention also provides a novel SP source locator method for identifying regions of the brain responsible for EP waveform translations and determining when those regions are dysfunctional. SP waveforms are recorded from a plurality of scalp electrodes disposed at various positions about the head of a subject. A set of such SP waveforms is shown in FIG. 7.

Figure 7:
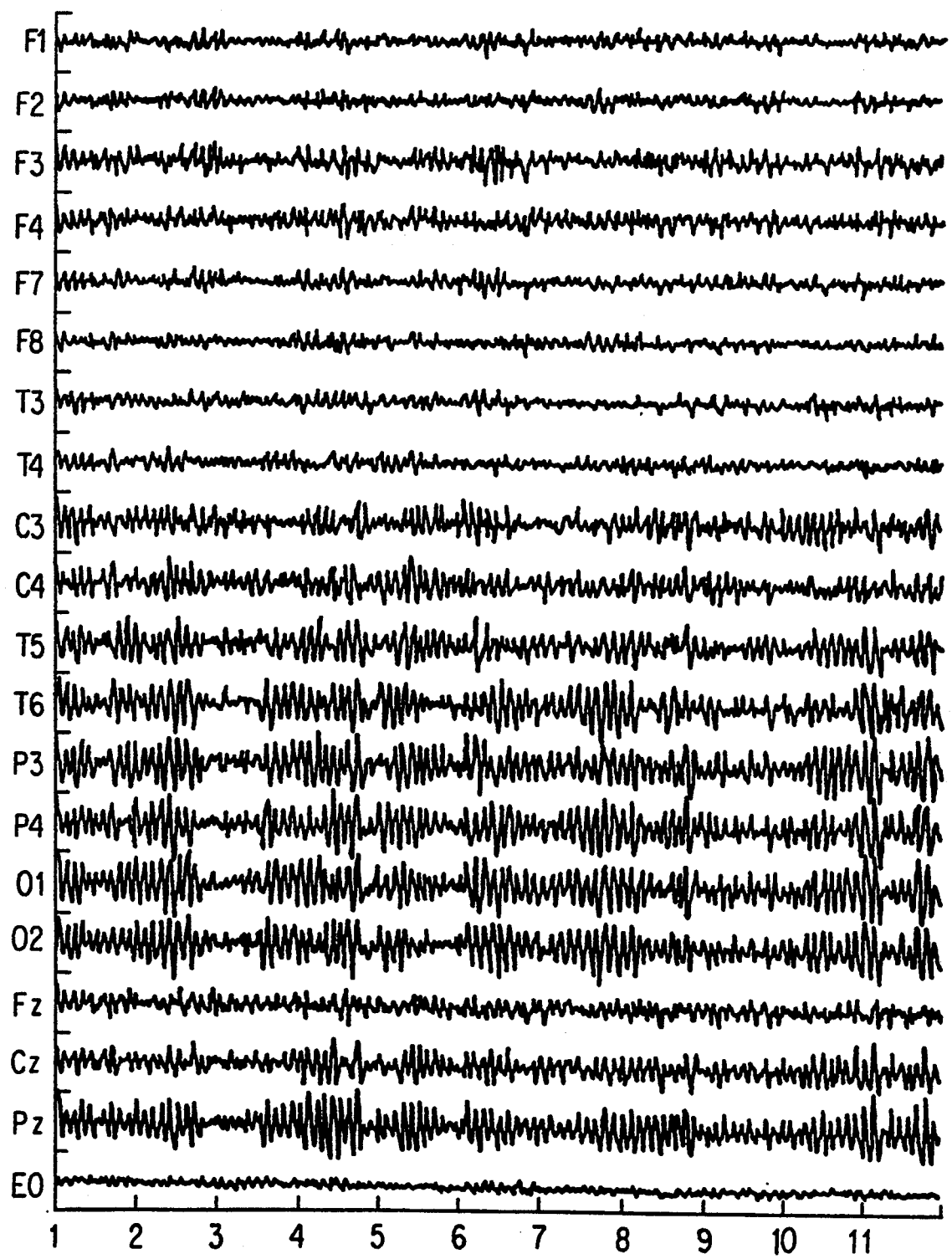
FIG. 7 shows a multi-channel recording of EEG (SP) data for a subject who is awake when the eyes of that subject are closed.

FIG. 7 shows 2.5 second recordings of EEG SP waveforms obtained from electrodes 3. Nineteen of electrodes 3 were attached to various regions of the head of subject 2. Also shown is a concurrent recording of the electro-occulogram (EO), which was used to identify eye movement artifacts. Labels on the left-hand side of the SP waveforms correspond to the positions on the head of subject 2 of each electrode 3 from which those waveforms were obtained. Odd numbered labels indicate that the corresponding electrode was at the left hemisphere and even numbered labels indicate that the corresponding electrode was at the right hemisphere. Labels having a "z" suffix indicate electrodes are located on the center of the midsagittal plane which exactly divides the left and right hemispheres of the brain. Labels that have a "f" prefix correspond to electrodes positioned on the scalp at regions adjacent to prefrontal, frontal, and premotor regions of the brain. Labels that have a "t" prefix correspond to electrodes positioned on the scalp adjacent to anterior-posterior temporal lobes of the brain. Labels that have a "c" prefix correspond to electrodes positioned on the scalp adjacent to sensory motor regions of the brain. Labels that have a "o" or "p" prefix correspond to electrodes positioned on the scalp at regions adjacent to the occipital and parietal regions of the brain, respectively.

The data shown in FIG. 7 was recorded while the eyes of subject 2 were closed and while subject 2 was relaxed and while no stimuli was being presented to subject 2. FIG. 7 shows SP waveforms and those waveforms have correlations (i.e., the waveforms are similar to one another).

Each of those SP waveforms is modelled as a linear superposition of three basis waveforms whose coefficients are the coordinate positions of the modelled SP waveforms. Preferably, a background corresponding to eye movement artifacts is initially subtracted from the SP waveforms. Mathematically, the three basis waveforms $f_1$, $f_2$, and $f_3$ are equated to each of the SP waveforms, $SP_i(x_i,y_i,z_i)$ for $i=1$ to the number of SP waveforms, N, recorded by electrodes at coordinates $(x_i,y_i,z_i)$, as:

$$SP_i(x_i,y_i,z_i) = x_i f_1 + y_i f_2 + z_i f_3 + K$$

where K is a constant function. The N linear equations of the model are used to provide the best solutions for the gradient waveform functions $f_1$, $f_2$, and $f_3$ (i.e., the solutions which provide the smallest errors between the SP waveforms and the linear combination of basis waveforms). The SP waveforms are then each represented by a linear combination of the basis waveform functions and coefficients for the representation which provide the closest approximation for each of the SP waveforms are determined. The determined coefficients for each of the electrode positions for the subject are compared with normative values of determined coefficients for the same electrode position determined from a large population of subjects. Large deviations from the normative determined coefficient values indicate a brain abnormality in the brain region of the subject which is adjacent to that electrode position.

Conventionally, axes extending from the left side of the head to the right side of the head, from the back of the head to the front of the head, and from the ventral to the dorsal positions of the head are represented by x, y, and z axes, respectively. The determined coefficients may be plotted in a three dimensional plot or in a 2 dimensional projection along a plane, with the determined coordinates plotted along the axes to which they correspond. We call those plots SP source locator plots.

A pattern exists in the SP source locator plot in which the relative positions of electrode plot position correspond roughly to relative positions of electrodes on the head of the subject. Furthermore, the relative position of points in the source locator plot are very similar for all subjects with normally functioning brains.

When positions of points in the three-dimensional space representing electrode positions on the head of a subject do not correspond to normative values (from a large population of subjects) of those positions, brain dysfunction in the region near the non-correlated electrodes is indicated.

Failure in brain function can be attributed to prior insults and trauma that resulted in disconnection syndrome such as when a portion of the brain is torn free from surrounding structures leaving that region of the brain to function independently without integration to the rest of the brain. When a brain region is isolated by injury and no longer connected to the remaining functions of the brain, that regions generates unique SP waveforms that primarily arise from the injured tissues. The source locator identifies those disconnected regions as statistical deviations from an expected distribution of critical functions within the x, y, and z SP gradient coordinate space. The source locator method provides information about pathological reasons for the failure of a subject to generate EP waveforms for particular perceptual, conceptual and emotional stimuli.

Expected distributions of determined coordinates in a source locator plot are based upon the means and standard deviations of sets of coefficients obtained from a normal population of human subjects. The determined coordinates for electrodes from individuals with brain dysfunction are compared to normative source locator plot data from normal subjects, by computing the statistical distance, i.e., variation in coordinates in source locator plot between source locator points for an individual and normative coordinates for a large population.

A deviation of a determined position for an individual from a normative value indicates that a region of the brain that is adjacent to the electrode for that source locator point is dysfunctional. Since functions of a dysfunctional region cannot properly be performed, EP signals which would result from translations performed in that portion of the brain may not occur. Since the stimulus model discussed above is only accurate when the brain performs translations corresponding to the model, it is useful to know which portions of the brain are dysfunctional in order to adjust the stimulus model.

FIG. 8A shows an average SP structure for representative recordings from 25 normal subjects with 2 recordings from each subject in which the SP waveforms for all electrodes 3 are represented by coefficients that locate their functional origin within the brain. Those coordinates comprise the normative SP structure for brains from normal populations. Those coordinates also closely approximate the relative positions of EEG electrodes 3 on the scalp of subject 2 during recording.

FIG. 8B shows an SP structure for a subject who had closed head trauma due to an automobile accident. FIG. 8B shows that the SP waveforms of electrodes F7 and T3 have low correlations with the three basis waveforms, and are extruded or disconnected from the overall SP structure.

Figure 8C:
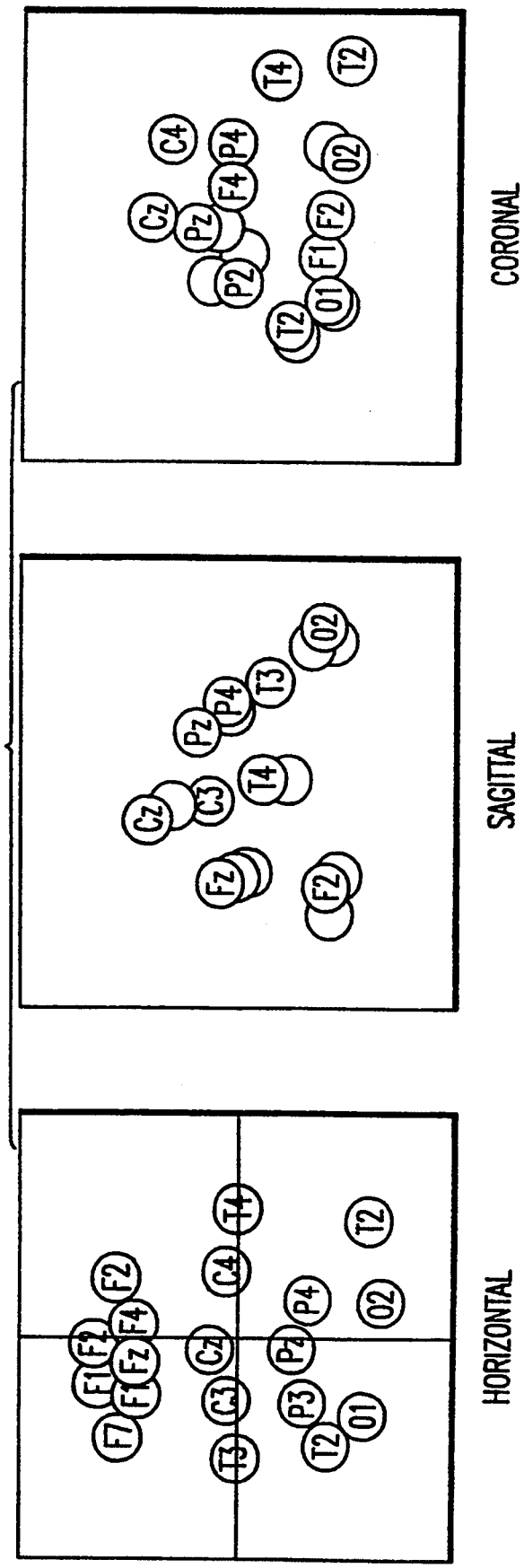

FIG. 8C shows an SP structure for a subject who had surgical resection of the right occipitoparietal area because of a tumor in that region. FIG. 8C shows that the SP waveforms for all electrodes in the right posterior lobe have low correlations with the three basis waveforms, and are disconnected from the overall SP structure.

At the present time, there are no other brain measurements that describe disconnection syndrome in the manner shown in FIGS. 8B and 8C. These measurements provide a significant key with which to determine why subject 2 cannot perform specific mental functions such as perception, conception, thinking and feeling. The presence of disconnected brain regions precludes training and the control of device interfaces by means of conception, conceptual thought or feeling. Such disconnection requires rehabilitation before neural control of a device interface is possible. The reconnection procedure described below provides a means for improving the connectivity between disconnected or dysfunctional regions of the brain and the remaining regions of the brain. Once reconnection has been effected, subject 2 may be trained to control a hardware device.

The present invention provides a novel method for using feedback in conjunction with the SP source locator method to train brain injured patients to rehabilitate dysfunctional mental functions. Similar to the technique called "neuro-muscular rehabilitation", the source locator feedback method coupled with feedback from controlled device 10 of the present invention allows brain injured patients to use feedback signals to indicate when connectivity between specific brain regions is high. That procedure allows the subject to discover and use mental strategies that yield high rates of feedback.

First, the SP source locator method is performed. Then, feedback corresponding to the correlation between source locator points and normative population points is presented to the subject. The SP source locator method is again performed and the results fed back to the subject via, for example, device 10. By trial and error, the subject uses that feedback to reduce the deviation between his or her individual source locator points and normative positions for those points.

When a dysfunctional region of the brain of a subject is so rehabilitated, it is not necessary to modify the stimulus model prior to performing EP evaluations for use of that model with a neurocybernetic control device.

The linear equations for basis vectors do not usually have an exact equality to the EP and SP waveforms, in the models discussed above. This is so because the data is real data with real variations from any model. Therefore solutions for the attribute waveforms, exemplar coefficients, SP source locator basis waveforms and SP source locator determined coefficients must take into account the inexact correspondence between the model and the data. The inexact nature of the correspondence is accounted for by finding a "best fit" between the model parameters mentioned above and the data. A best fit maximizes correlation or equivalently minimizes deviations between the modelled values of the SP and EP waveforms and the actual recorded values for them. One way to minimize deviations is to use a least squares analysis to minimize the sum of the squared differences between model values for waveforms and the recorded waveforms.

Correlation maximization may also be used to provide a best fit. Pearson product-moment correlations are used with both raw unfiltered, and with filtered SP waveforms. Filtered waveforms are raw SP waveforms decomposed into four well known frequently bands: the $\delta$ band from 3.5 to 7 Hz, the $\theta$ band from 3.5 to 7 Hz, the $\alpha$ band from 7 to 13 Hz and the $\beta$ band from 13 to 30 Hz. The method yields a triangular matrix of correlation coefficients that describe the relative similarities and dissimilarities in raw or filtered SP waveforms for all combinations of electrode positions.

The five triangular matrices (four frequency bands plus the original data set) may be analyzed to provide source locator plot data. Each matrix is decomposed and modeled as a linear combination of three orthogonal basis waveforms. The three orthogonal basis waveforms represent three anatomical directions (anterior-posterior, dorsal-ventral, and lateral directions) and along with the determined coefficients are determined as discussed above.

The present invention provides a determination of basis waveforms and coefficient for anatomical/functional family membership of SP waveforms from a plurality of scalp locations and also perceptual or conceptual family membership of EP waveforms from a plurality of perceptual conceptual or emotional attributes of stimuli. Both of those types of determination require solution of a set of linear equations which are equated to real data and are therefore, strictly speaking, not equations but correlations or best fits to the data, and types of determinations use identical algorithms for their solution. Those types of equations may be solved using methods generally called factor analysis and preferably the specific factor analysis methods called principal components analysis (PCA) which are well known. A complete discussion of factor analysis including its theory and implementation, including FORTRAN program listings can be found in "*Introduction to Modern Factor Analysis*" (Guertin and Bailey, 1970, Edward Brothers Inc., Ann Arbor, Mich.), and in particular the PRINCO PCA program on pp. 116–118, the discussion of PCA on pp. 30–33 and 96–102, and in "*Multivariant Data Analysis*" (1971, Wiley & Sons Inc., New York, N.Y.), which also describes PCA. Those books are incorporated herein by reference. The PRINCO PCA program has been included at the end of this specification in Appendix II, for convenience.

Assuming we want to describe waveforms, the definitions for N, M, & L of the PRINCO routine are:

N = number of EP or SP waveforms (R = correlation matrix and is N×N; LI=0 for full rank); and M = number of digitized points in an EP/SP waveform record.

L = number of basis waveforms to return.

The PCA method is used in the same way for both SP and EP waveforms, the only distinction being that preferred SP waveforms are long records of greater than 1 minute duration and are recorded from a plurality of scalp positions, while preferred EP waveforms are short records of between 0.5 and 1 second in duration. For both SP and EP data of the present invention PCA provides a "best fit" to the data.

A description of PCA in the context of the present invention is presented below. Let $W_i$ equal the number of waveforms which represents the number of electrodes in an SP analysis and which represents the number of stimuli in an EP analysis.

$W_i$ for $i=1, \ldots, N$, represents a set of N waveforms. The N waveforms are stored in a computer. A correlation matrix, such as a Pearson matrix, is formed by correlating each of the N waveforms with every other one of the N waveforms.

The correlation matrix is factored using a standard PCA computer program to obtain k orthogonal basis waveforms $C_j$ or $J=1, \ldots, k$, that are sufficient to represent at least 85% of the variability in correlations among all the electrode waveforms according to equations 3 and 4. Each of the N waveforms has a correlation with each of the k basis waveforms. The correlation coefficient between a basis waveform and one of the N waveforms stored in memory defines the contribution of that basis waveform to the waveforms stored in memory and, for the ith waveform stored in memory and the jth basis waveform is defined to be $a_{ij}$. Thus, if $a_{i1}$ is the contribution from the component $C_1$ (i.e., where $C_i$ is the first basis waveform), and $a_{i2}$ is the contribution for the component $C_2$ (i.e., where $C_2$ is the second basis waveform), then:

$$W_1 = a_{11}C_1 + a_{12}C_2 + a_{13}C_3 \ldots a_{1k}C_k \quad \text{(Eq. 2)}$$
$$W_2 = a_{21}C_1 + a_{22}C_2 + a_{23}C_3 \ldots a_{2k}C_k$$
$$\cdot$$
$$\cdot$$
$$\cdot$$
$$W_N = a_{N1}C_1 + a_{N2}C_2 + a_{N3}C_3 \ldots a_{Nk}C_k$$

In the case of N SP waveforms for N electrodes, $k=3$, which is the number of anatomical directions (the anterior-posterior direction, the lateral direction, and the dorsal-ventral direction). In the case of N EP waveforms for an N-stimulus set, k equals the number of attributes which is one less than the dimensionality of the basis set due to the background basis vector.

FIGS. 8A–8C show results of an SP analysis using multichannel recordings of SP waveforms to compute SP structures for a normal brain, for a brain with left fronto-temporal damage, and for a brain with right posterior disconnection, respectively. Each of FIGS. 8A–8C presents two-dimensional projections onto standard neuroanatomical planes: the horizontal plane comprising the anterior-posterior and lateral directions; the sagittal plane along the anterior-posterior and dorsal-ventral directions and the coronal plane along the dorsal-ventral and lateral directions.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A system for acquiring EEG waveforms from a subject and interpreting those waveforms to indicate what the subject is experiencing or thinking, comprising:
   means for recording brainwave EEG waveforms from the subject;
   means, coupled to said means for recording, for representing a brainwave EEG waveform that has been recorded by the means for recording as a linear combination of a set of basis waveforms, said linear combination consisting of a weighted sum of all members of the set of basis waveforms in which each member of the set of basis waveforms is weighted by a weighting coefficient;
   means, coupled to said means for representing, for corresponding thought attributes to members of the set of basis waveforms, a first thought attribute corresponding to a first basis waveform of the set of basis waveforms;
   means, coupled to said means for representing, for corresponding each member of a set of thought exemplars for the first thought attribute to a different thought exemplar range of weighting coefficient values for the first basis waveform than any other member of the set of thought exemplars, a first thought exemplar range of weighting coefficients corresponding to a first thought exemplar of the first basis waveform for the first thought attribute;
   means, coupled to said means for representing, said means for corresponding thought attributes, and said means for corresponding each member of a set, for determining when the first thought exemplar range includes a weighting coefficient of said linear combination for the first basis waveform;
   means, coupled to said means for determining, for generating a thought signal indicating when said weighting coefficient is in the first thought exemplar range;
   a device for performing a specified function in response to a thought by the subject;
   a controller interface, coupled to said means for generating and to the device, for converting said thought signal into a control signal for controlling the functioning of the device.

2. A system according to claim 1, further comprising:
   means, coupled to the means for recording, for presenting stimuli of the stimulus model to said subject.

3. A system according to claim 1, further comprising:
   means, coupled to the means for recording, for repetitively presenting a brief first stimuli to the subject;
   means, coupled to the means for recording and the means for repetitively presenting, for controlling presentation of the first stimuli to the subject; and
   means, coupled to the means for recording and the means for repetitively presenting, for synchronizing presentation of the first stimuli with recording of brainwave EEG waveforms that comprise EP type signals.

4. A system according to claim 1, wherein:
   said means for recording comprises an EEG electrode, an analog to digital converter coupled to the EEG electrode, said analog to digital converter functioning by converting a signal provided by the EEG electrode into digital form, a digital CPU coupled to the analog to digital converter, and memory means coupled to the digital CPU.

5. A system according to claim 4, wherein said means for corresponding each member of a set of thought exemplars further comprises:
   means for determining correlation values between said brainwave EEG waveform and members of the set of basis waveforms.

6. A system according to claim 4, further comprising an eyeglass frame on which is mounted said means for repetitively presenting.

7. A system according to claim 1, wherein said means for recording comprises EEG electrodes that are connected to an EEG amplifier, an analog to digital converter having an input that is connected to an output of EEG amplifier, and a memory medium that is coupled to said analog to digital converter for storing digital signals provided by the analog to digital converter.

8. A system according to claim 7, further comprising a central processing unit that is coupled to said analog to digital converter and to said memory medium.

9. A system according to claim 8, wherein said means for generating a thought signal comprises an interface that is connected to said central processing unit.

10. A system according to claim 9, further comprising:
   means, coupled to the means for recording, for repetitively presenting a brief first stimuli to the subject, said means for repetitively presenting comprising a transducer;
   wherein said means for repetitively presenting is coupled to and controlled by said central processing unit.

11. A system according to claim 10, further comprising an eyeglass frame on which is mounted said means for repetitively presenting.

12. A system according to claim 1, wherein said means for recording comprises EEG electrodes that are connected to an EEG amplifier, an analog to digital converter having an input that is connected to an output of said analog to digital converter, and a memory medium, and further comprising:

a central processing unit that is connected to said analog to digital converter;

a display monitor that is connected to and controlled by said central processing unit; and means, coupled to the central processing unit, for displaying indicia of the thought exemplars of the thought attributes that correspond to members of the set of basis waveforms.

13. A method for acquiring and decoding EEG waveforms from a subject to determine what the subject is thinking, comprising:

recording brainwave EEG waveforms from the subject;

providing a stimulus model representing attributes of stimuli as basis vectors of a vector space and representing exemplars of each attribute as magnitudes for the corresponding basis vectors;

interpreting said EEG waveforms according to a stimulus model in terms of the attributes and the exemplars of the model to determine waveforms corresponding to the attributes and the exemplars.

14. A method for determining attribute waveforms and exemplar coefficients for stimuli of a stimulus set for a subject, comprising the steps of:

modelling the attributes as basis vectors of a vector space and modelling exemplars of an attribute as coefficients for that attribute;

presenting stimuli of the stimulus set to the subject; recording EEG signals from the subject during the step of presenting stimuli of the stimulus set to the subject, thereby providing recorded EEG signals from the subject;

corresponding each of the recorded EEG signals, to a linear combination of the basis vectors whose coefficients represent exemplars associated with the first stimuli;

determining coefficients and basis vectors representing exemplars and attributes, respectively, which provide a best fit to the recorded EEG signals.

15. A method according to claim 14, wherein the step of determining coefficients and basis vectors representing exemplars and attributes, respectively, which provide a best fit to the recorded EEG signals comprises the step of performing principle components analysis upon the linear combinations of basis vectors and recorded EEG signals from the subject.

16. A system for acquiring EEG waveforms from a subject and interpreting those waveforms to indicate what the subject is thinking, comprising:

first means for recording brainwave EEG waveforms that comprise EP type EEG signals from the subject, comprising an EEG electrode;

second means for repetitively presenting a brief first stimuli to the subject;

third means, coupled to the first means and to the second means, for controlling presentation of the first stimuli to the subject;

fifth means for synchronizing presentation of the first stimuli with recording of said brainwave EEG waveforms by the first means; and sixth means, coupled to the third means, for presenting second stimuli to said subject during presentation of the first stimuli to the subject by the third means.

17. A system for assisting in diagnosis of brain dysfunction in a subject, comprising:

first means for concurrently recording N brainwave SP waveforms labelled $SP_i$ fir $i=1 \ldots N$ from N locations at coordinates $x_i, y_i, z_i$ on the scalp of the subject, comprising EEG transducers;

second means, coupled to the first means, for determining three basis waveforms $f_1$, $f_2$, and $f_3$ which provide the best fit of the function $F_i(x_i, y_i, z_i)$ to the $SP_i$ waveforms, wherein:

$$F_i(x_i, y_i, z_i) = x_i f_1 + y_i f_2 + z_i f_3 + K$$

where K is a waveform having a constant value;

third means, coupled to the second means, for determining N sets of determined coefficients $x1_i$, $y1_i$, $z1_i$, which each minimize a difference between $F_i$ and $SP_i$;

fourth means, coupled to the third means, for storing a jth set of normative values for determined coefficients; and fifth means, coupled to the third means, for comparing a jth set of the N sets of said determined coefficients for a jth location $x_j$, $y_j$, $z_j$, on the scalp of the subject with the jth set of normative values for determined coefficients, wherein normative values are average values determined from a large population of subjects and said jth set of normative values are determined coefficients at scalp locations of the large population which correspond to said jth location on the scalp of the subject;

means, coupled to the fifth means, for determining when differences between said jth set of said determined coefficients and said jth set of normative values are larger than predetermined differences;

wherein differences between said jth set of said determined coefficients and said jth set of normative values which are larger than predetermined differences indicate brain dysfunction in a region of the brain that is adjacent to the jth location.

18. A method for assisting in diagnosis of brain dysfunction in a subject, comprising:

concurrently recording N brainwave SP waveforms labelled $SP_i$ for $i=1 \ldots N$ from N locations at coordinates $x_i, y_i, z_i$ on the scalp of the subject, comprising EEG transducers;

determining three basis waveforms $f_1$, $f_2$, and $f_3$ which provide the best fit of the function $F_i(x_i, y_i, z_i)$ to the $SP_i$ waveforms, wherein:

$$F_i(x_i, y_i, z_i) = x_i f_1 + y_i f_2 + z_i f_3 + K$$

where K is a waveform having a constant value;

determining N sets of determined coefficients $x1_i$, $y1_i$, $z1_i$, which each minimize a different between $F_i$ and $SP_i$; and storing a jth set of normative values for determined coefficients;

comparing a jth set of the N sets of said determined coefficients for a jth location $x_j$, $y_j$, $z_j$, on the scalp of the subject with the jth set of normative values for determined coefficients, wherein said normative values are average values determined from a large population of subjects and said jth set of normative values are determined coefficients at scalp locations of the large population which correspond to said jth location on the scalp of the subject, determining when differences between said jth set of said determined coefficients and said jth set of normative values are larger than predetermined differences;

wherein differences between said jth set of said determined coefficients and said jth set of normative values which are larger than predetermined differences indicate brain dysfunction in a region of the brain that is adjacent to the jth location.

* * * * *